United States Patent [19]

Okino et al.

[11] Patent Number: 5,879,945
[45] Date of Patent: Mar. 9, 1999

[54] METHOD FOR MEASURING OXIDATION-REDUCTION POTENTIAL IN A FLUE GAS DESULFURIZATION PROCESS

[75] Inventors: Susumu Okino; Hiroshi Tanaka; Koosoo Tao, all of Hiroshima-ken, Japan

[73] Assignee: Mitsubishi Heavy Industries, Ltd., Tokyo, Japan

[21] Appl. No.: 916,251

[22] Filed: Aug. 22, 1997

[30] Foreign Application Priority Data

Aug. 23, 1996 [JP] Japan .................................. 8-222040

[51] Int. Cl.$^6$ ........................................... G01N 27/00
[52] U.S. Cl. ............................ 436/55; 436/137; 436/175
[58] Field of Search .................. 423/243.01, 243.03, 423/243.08, DIG. 5; 422/110, 62, 93; 436/175, 55, 137, 904

[56] References Cited

U.S. PATENT DOCUMENTS

| 4,416,786 | 11/1983 | Knorre et al. ........................... 210/746 |
| 4,938,838 | 7/1990 | Dalin et al. ............................... 156/627 |
| 5,266,286 | 11/1993 | Ukawa et al. ....................... 423/243.08 |
| 5,433,936 | 7/1995 | Ukawa et al. ....................... 423/243.01 |
| 5,560,893 | 10/1996 | Okino et al. .......................... 423/242.1 |
| 5,595,713 | 1/1997 | Gohara et al. ........................... 422/170 |

FOREIGN PATENT DOCUMENTS

| 07204459 | 8/1995 | Japan . |
| 08024566 | 1/1996 | Japan . |

*Primary Examiner*—Jeffrey Snay
*Attorney, Agent, or Firm*—Foley & Lardner

[57] ABSTRACT

In a flue gas desulfurization process based on the wet lime-gypsum method, the controlled oxidation of sulfites, by comparison of the redox potential of an absorbing fluid in a sample tank and the redox potential of the absorbing fluid in a completely oxidized state in a reference tank, and adjustment of the rate of air flow through the absorbing fluid, is improved by removing peroxides from the absorbing fluid in the reference tank before passing air therethrough to effect oxidization to a completely oxidized state. The method avoids instability due to the presence of peroxides in the absorbing fluid.

3 Claims, 3 Drawing Sheets

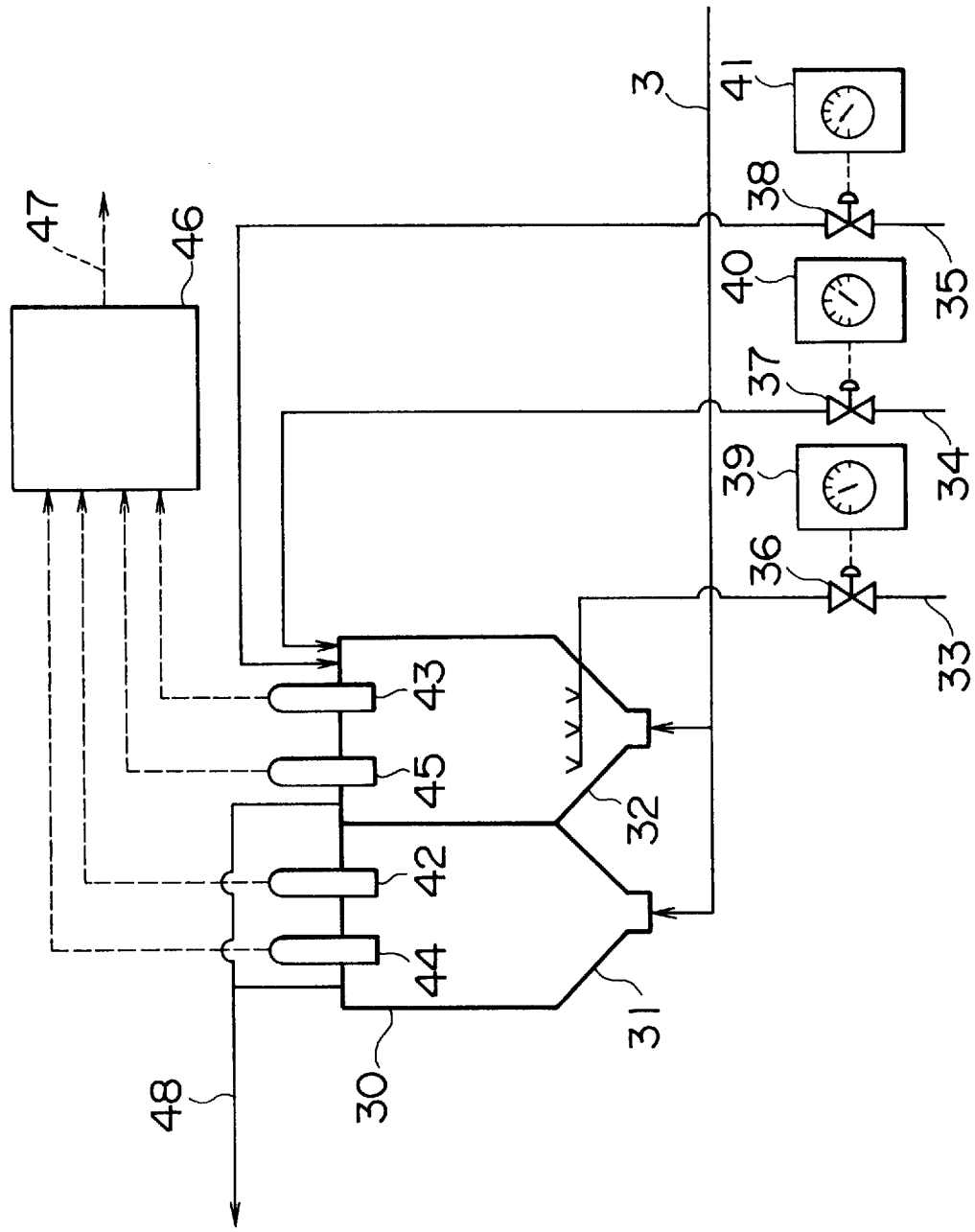
F I G. 1

METHOD FOR MEASURING OXIDATION-REDUCTION POTENTIAL IN A FLUE GAS DESULFURIZATION PROCESS

BACKGROUND OF THE INVENTION

1. Field of the Invention

This invention relates to a method for measuring oxidation-reduction potential in a flue gas desulfurization process which method is adaptable for use with a method for controlling the oxidation of sulfites in a flue gas desulfurization process wherein the oxidation of calcium sulfite in an absorbing fluid can be achieved efficiently.

2. Description of the Related Art

When exhaust gas containing sulfur oxides is subjected to flue gas desulfurization according to the wet lime-gypsum method, sulfur dioxide which is a predominant sulfur oxide present in the exhaust gas is brought into contact with an absorbing fluid containing calcium carbonate and absorbed according to the following reaction.

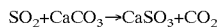

$$SO_2 + CaCO_3 \rightarrow CaSO_3 + CO_2$$

A portion of the calcium sulfite so produced is oxidized by oxygen present in the exhaust gas to form gypsum, as represented by the following reaction formula.

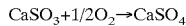

$$CaSO_3 + 1/2 O_2 \rightarrow CaSO_4$$

Usually, the oxygen concentration in the exhaust gas is so low that the oxidation of calcium sulfite to gypsum is not sufficiently effected. Accordingly, an oxygen-containing gas is supplied from the outside of the system and passed through the absorbing fluid.

However, if the flow rate of the oxygen-containing gas is low, the concentration of unoxidized calcium sulfite will increase. This may cause several difficulties including an inhibition of the dissolution of calcium carbonate used as the absorbent, a reduction in desulfurization performance, and an increase in the chemical oxygen demand (hereinafter referred to as "COD") of waste water from the desulfurizer.

On the other hand, if an attempt is made to maintain a high degree of conversion of calcium sulfite to gypsum, it is inevitable to supply the oxygen-containing gas in excess with consideration for load fluctuations and the like. This leads to an increase in running cost and a rise in the COD of waste water.

Accordingly, it is necessary to control the flow rate of the oxygen-containing gas so as to remain in a proper range.

In order to control the flow rate of the oxygen-containing gas involved in the oxidation of calcium sulfite, a method based on the use of oxidation-reduction potential (hereinafter referred to as "ORP") is known. In the conventional method for controlling the flow rate in response to ORP, a preset ORP value is determined in advance on the basis of the preestablished relationship between ORP and sulfurous acid concentration, and the flow rate is controlled in response to a deviation signal between a signal obtained by detecting the ORP of the absorbing fluid continuously and the preset ORP value.

However, ORP is affected not only by sulfurous acid concentration, but also by pH and dissolved solution components. Consequently, the conventional method has the disadvantage that stable oxidation control cannot be achieved because of variation in pH and changes of dissolved solution components, which result from load fluctuations, changes of the absorbent material, and/or changes of the type of fuel, as well as erroneous indications of the pH meter. This may cause such difficulties as an increase in the COD of waste water due to an increase in sulfurous acid concentration or an oversupply of air.

In order to overcome these disadvantages, the present inventors have developed an oxidation controlling method which comprises continuously detecting a first deviation signal between the ORP of the absorbing fluid and the ORP of the absorbing fluid in a completely oxidized state by means of an ORP detector equipped with a sample fluid tank for detecting the ORP of the absorbing fluid and a reference fluid tank for oxidizing the absorbing fluid by the passage of air therethrough and detecting the ORP of the absorbing fluid in a completely oxidized state, and controlling the flow rate of the oxygen-containing gas in response to a second deviation signal between the first deviation signal and a preset ORP deviation value (Japanese Patent Provisional Publication No. 24566/1996).

One example of an ORP detector constructed on the basis of this method is illustrated in FIG. 3, and the method for measuring ORP is described below with reference to this figure. From an absorption tower where combustion exhaust gas is brought into contact with an absorbing fluid containing a calcium compound, a portion of absorbing fluid 3 is introduced into an ORP measuring tank 17. ORP measuring tank 17 is partitioned into a sample fluid tank 18 and a reference fluid tank 19. In reference fluid tank 19, the absorbing fluid is completely oxidized by supplying air 20 from the outside of the system. In these tanks 18 and 19, the ORP of the absorbing fluid and the ORP of the absorbing fluid in a completely oxidized state are detected by ORP electrodes 21 and 22, respectively. The detected signals are fed to an arithmetic unit 23 where the deviation between the ORP of the absorbing fluid and the ORP of the absorbing fluid in a completely oxidized state is calculated. A deviation signal 24 representing this deviation is delivered from arithmetic unit 23. After ORP measurements are made, the return absorbing fluid from sample fluid tank 25 and the return absorbing fluid from reference fluid tank 26 are returned again to the fluid reservoir of the absorption tower.

In this method, the ORP of the absorbing fluid is continuously detected in one (i.e., sample fluid tank 18) of the two tanks into which the ORP measuring tank is partitioned. In the other tank (i.e., reference fluid tank 19), the ORP of the absorbing fluid in a completely oxidized state is continuously measured by constantly passing air through the absorbing fluid placed therein. However, since peroxides may be present in the absorbing fluid according to the operating condition of the desulfurizer, the values obtained by passing air through the absorbing fluid and measuring the ORP of the absorbing fluid in a completely oxidized state become unstable. This may interfere with the maintenance of stable oxidation control and cause such difficulties as an increase in the COD of waste water due to an oversupply of air.

SUMMARY OF THE INVENTION

In view of the above-described technical level, an object of the present invention is to provide a method for measuring oxidation-reduction potential which is adaptable for use with a method for controlling the oxidation of sulfites in a flue gas desulfurization process for treating exhaust gas containing sulfur oxides according to the wet lime-gypsum method, and which can overcome the disadvantages of the conventional methods.

As described above, in a flue gas desulfurization process for treating exhaust gas containing sulfur oxides according to the wet lime-gypsum method, the flow rate of an oxygen-containing gas passed through the absorbing fluid has conventionally been controlled by detecting a first deviation signal between the ORP of the absorbing fluid and the ORP of the absorbing fluid in a completely oxidized state by means of an ORP detector equipped with a sample fluid tank for detecting the ORP of the absorbing fluid and a reference fluid tank for oxidizing the absorbing fluid by the passage of air therethrough and detecting the ORP of the absorbing fluid in a completely oxidized state, and controlling the flow rate of the oxygen-containing gas in response to a second deviation signal between the first deviation signal and a preset ORP deviation value. However, if the absorbing fluid is completely oxidized by blowing air thereinto without decomposing peroxides present therein, the ORP of the absorbing fluid in a completely oxidized state may vary. The present inventors have now discovered that this problem can be solved by employing a method in which peroxides present in the absorbing fluid are reductively decomposed before passing air therethrough. The present invention has been completed on the basis of this discovery.

In order to accomplish the above object, the present invention provides, in a flue gas desulfurization process wherein exhaust gas containing sulfur oxides is treated with an absorbing fluid containing a calcium compound, and an oxygen-containing gas is passed through the absorbing fluid containing the resulting calcium sulfite to oxidize the calcium sulfite and thereby form gypsum, a method for measuring oxidation-reduction potential that is adaptable for use with a method for controlling the oxidation of sulfites which comprises the steps of detecting a first deviation signal between the oxidation-reduction potential of the absorbing fluid and the oxidation-reduction potential of the absorbing fluid in a completely oxidized state by means of an oxidation-reduction potential detector equipped with a sample fluid tank for detecting the oxidation-reduction potential of the absorbing fluid and a reference fluid tank for oxidizing the absorbing fluid by the passage of air therethrough and detecting the oxidation-reduction potential of the absorbing fluid in a completely oxidized state, and controlling the flow rate of the oxygen-containing gas in response to a second deviation signal between the first deviation signal and a preset oxidation-reduction potential deviation value, characterized in that the oxidation-reduction potential of the absorbing fluid in a completely oxidized state is measured by decomposing peroxides present in the absorbing fluid with the aid of a chemical agent and thereafter passing air through the absorbing fluid.

In one preferred embodiment of the present invention, peroxides present in the absorbing fluid are decomposed by adding thereto hydrogen peroxide and then an acid.

In another preferred embodiment of the present invention, peroxides present in the absorbing fluid are decomposed by using a reducing agent selected from the group consisting of $SO_2$ gas, hydroxylammonium chloride ($NH_3OH$)Cl (also called hydroxylamine hydrochloride $NH_2OH.HCl$), an aqueous solution of sulfurous acid, a salt of sulfurous acid, and mixtures thereof, instead of adding hydrogen peroxide and an acid.

As described above, the present invention relates to, for use in a flue gas desulfurization process wherein exhaust gas containing sulfur oxides is treated with an absorbing fluid containing a calcium compound, and an oxygen-containing gas is passed through the absorbing fluid containing the resulting calcium sulfite to oxidize the calcium sulfite and thereby form gypsum, a method for controlling the oxidation of sulfites which comprises the steps of detecting a first deviation signal between the oxidation-reduction potential of the absorbing fluid and the oxidation-reduction potential of the absorbing fluid in a completely oxidized state by means of an oxidation-reduction potential detector equipped with a sample fluid tank for detecting the oxidation-reduction potential of the absorbing fluid and a reference fluid tank for oxidizing the absorbing fluid by the passage of air therethrough and detecting the oxidation-reduction potential of the absorbing fluid in a completely oxidized state, and controlling the flow rate of the oxygen-containing gas in response to a second deviation signal between the first deviation signal and a preset oxidation-reduction potential deviation value. According to the present invention, the first deviation signal between the oxidation-reduction potential of the absorbing fluid and the oxidation-reduction potential of the absorbing fluid in a completely oxidized state is detected by measuring the oxidation-reduction potential of the absorbing fluid in a completely oxidized state by adding a reducing agent to the reference fluid tank of the oxidation-reduction potential detector so as to decompose peroxides present in the absorbing fluid and thereafter passing air through the absorbing fluid.

The present invention will be more specifically described hereinbelow in connection with one embodiment thereof. It is to be understood that the present invention provides a method for decomposing peroxides present in an absorbing fluid for use in a flue gas desulfurization process and thereby determining a correct complete oxidation-reduction potential, thus making it possible to reduce the COD of waste water.

BRIEF DESCRIPTION OF THE DRAWINGS

FIG. 1 is a schematic view illustrating the construction of an exemplary ORP detector in accordance with the present invention;

DETAILED DESCRIPTION OF PREFERRED EMBODIMENTS

One embodiment of the present invention is described below. The present invention has been completed as a result of intensive investigations made with a view to achieving proper oxidation control in response to ORP, and is based on the discovery that, when the ORP of the absorbing fluid in a completely oxidized state is measured simply by passing air therethrough, the attained complete oxidation potential may vary owing to oxides and peroxides present prior to oxidation. In the method of the present invention, the oxidation-reduction potential of the absorbing fluid in a completely oxidized state is detected by passing air through the absorbing fluid after adding an aqueous solution of sulfurous acid to decompose peroxides by reduction or after adding an aqueous solution of hydrogen peroxide and then adding sulfuric acid to reduce the pH temporarily and thereby effect the reduction (or decomposition) of peroxides with hydrogen peroxide. Thus, peroxides present in the absorbing fluid are prevented from exerting an influence on the oxidation-reduction potential and, therefore, the oxidation-reduction potential of the absorbing fluid and the oxidation-reduction potential of the absorbing fluid in a completely oxidized state can be detected correctly. This makes it possible to maintain stable oxidation control and thereby reduce the COD of waste water.

Figure 2:
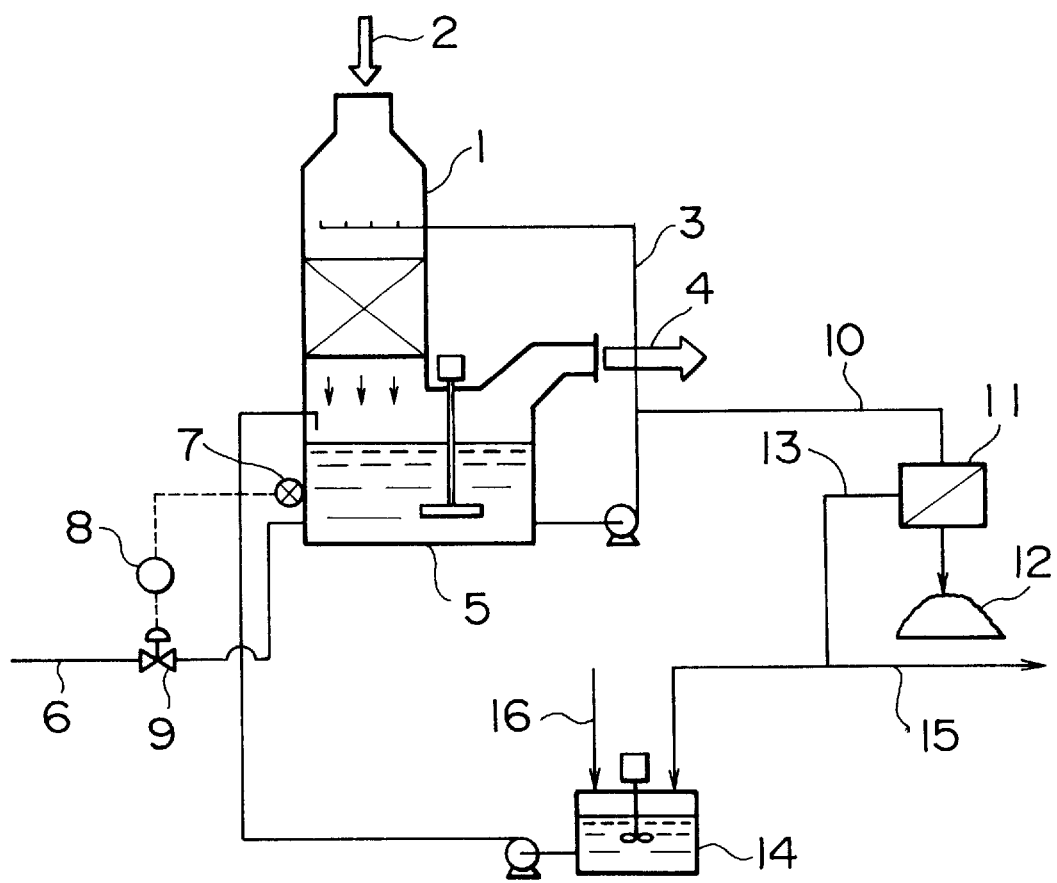
FIG. 2 is a schematic view illustrating an exemplary flue gas desulfurization process to which the method of the present invention is applied.
Figure 3:
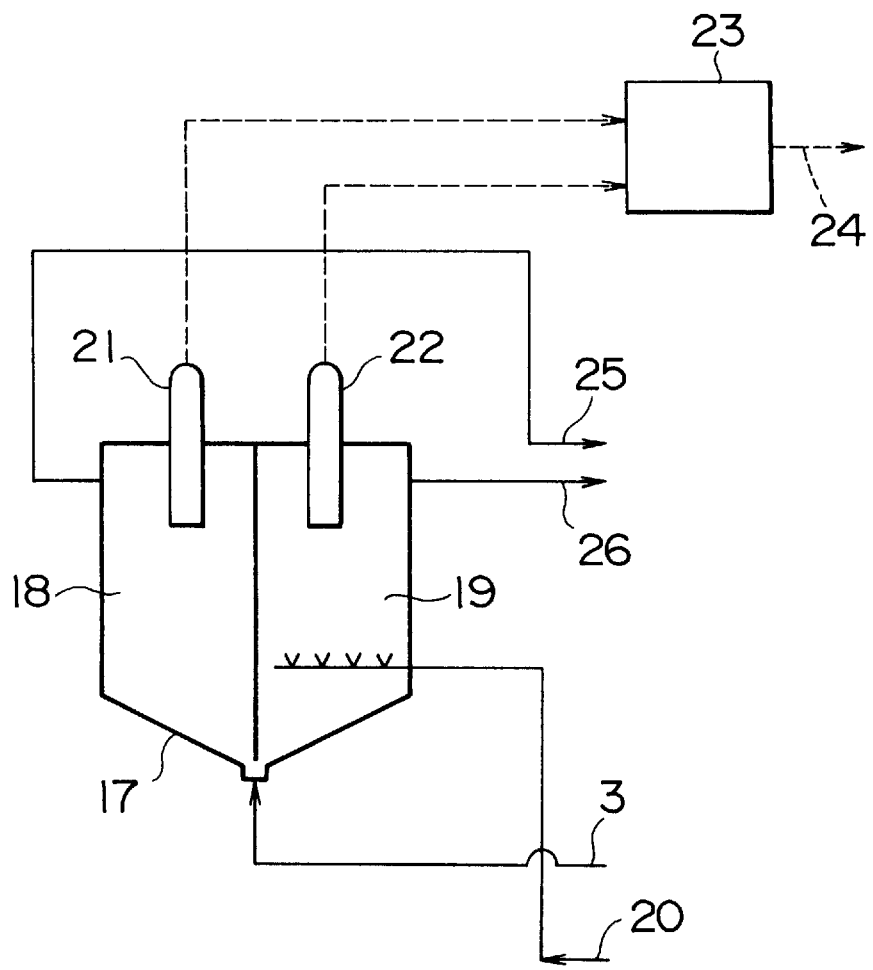
FIG. 3 is a schematic view illustrating the construction of an exemplary ORP detector partitioned into a sample fluid tank and a reference fluid tank.

One embodiment of the present invention is described below with reference to FIG. 2. FIG. 2 is a schematic view illustrating an exemplary flue gas desulfurization process to which the method of the present invention is applied. In the process of FIG. 2, combustion exhaust gas 2 introduced into an absorption tower 1 is brought into gas-liquid contact with an absorbing fluid 3 circulating through the absorption tower, so that sulfur oxides present in the combustion exhaust gas are absorbed and separated. The combustion exhaust gas from which sulfur oxides have been removed is discharged as purified gas 4. The sulfur oxides absorbed into absorbing fluid 3 are converted to calcium sulfite, part of which is oxidized by oxygen present in the combustion exhaust gas to form gypsum. Unoxidized calcium sulfite present in the absorbing fluid is oxidized by air (as an oxygen-containing gas) 6 passed through a fluid reservoir 5 of the absorption tower to form gypsum.

Since the gypsum so formed has low solubility, it precipitates from the absorbing fluid in the form of a solid. Part of the absorbing fluid containing gypsum is withdrawn from absorption tower 1 by way of a withdrawal line 10, and separated into gypsum 12 and filtrate 13 by means of a solid-liquid separator 11. Part of the resulting filtrate 13 is fed to a raw material preparation tank 14, and the remainder is discharged from the system as waste water 15. In raw material preparation tank 14, the filtrate is replenished with calcium carbonate 16 and returned again to absorption tower 1.

The above-described oxidation control is carried out in the following manner. A first deviation signal between the ORP of the absorbing fluid and the ORP of the absorbing fluid in a completely oxidized state, which are detected by an ORP detector 7, is fed to a flow rate controller 8. This flow rate controller 8 produces a control valve opening/closing signal in response to a second deviation signal between the first deviation signal and a preset ORP deviation value determined in advance on the basis of the relationship between known sulfurous acid concentrations and ORP values (i.e., the deviation between the ORP of the absorbing fluid and the ORP of the absorbing fluid in a completely oxidized state at a preset sulfurous acid concentration). The flow rate of air used as an oxygen-containing gas is regulated by controlling a control valve 9 in response to this opening/closing signal.

Now, the method for measuring the ORP of the absorbing fluid and the ORP of the absorbing fluid in a completely oxidized state is explained with reference to FIG. 1 illustrating the construction of an exemplary ORP detector in accordance with the present invention. A portion of absorbing fluid 3 is introduced into an ORP measuring tank 30. In this embodiment, ORP measuring tank 30 is partitioned into tank A 31 and tank B 32. Tank A 31 is a sample fluid tank for measuring the ORP of the absorbing fluid, while tank B 32 is a reference fluid tank for oxidizing the absorbing fluid by the supply of air 33 from the outside of the system and measuring the ORP of the absorbing fluid in a completely oxidized state.

First of all, a valve 37 is opened to inject an aqueous solution of hydrogen peroxide into tank B 32. Subsequently, a valve 38 is opened to inject a sulfuric acid solution 35 into tank B 32. After the lapse of a certain period of time, a valve 36 is opened to pass air 33 through tank B 32. Then, the ORP and pH of the absorbing fluid are measured with an ORP electrode 42 and a pH meter 44, respectively, while the ORP and pH of the absorbing fluid in a completely oxidized state are measured with an ORP electrode 43 and a pH meter 45, respectively.

ORP and pH signals detected in this state are fed to an arithmetic unit 46 where the deviation between the ORP signals is calculated to produce a deviation signal 47 between the ORP of the absorbing fluid and the ORP of the absorbing fluid in a completely oxidized state. This deviation signal 47 is sent to flow rate controller 8 (FIG. 2), by which control valve 9 is operated to control the flow rate of air 6 used as an oxygen-containing gas. The relationship between pH and ORP has been formulated and is used in arithmetic unit 46 for purposes of correction.

During this process, peroxides present in the absorbing fluid within tank B 32 are reductively decomposed, so that the influence of such peroxides on the oxidation-reduction potential can be prevented.

Thus, the ORP of the absorbing fluid is measured in tank A 31, while the ORP of the absorbing fluid in a completely oxidized state is measured in tank B 32.

The added amounts of the aqueous solution of hydrogen peroxide and the sulfuric acid solution, and the times for starting and terminating the passage of air may be automatically controlled with the aid of timers 39, 40 and 41 according to the results of experiments performed in advance.

The absorbing fluid 48 withdrawn from ORP measuring tank 30 is returned again to fluid reservoir 5 of the absorption tower.

Calculations of the above-described deviations are made according to the following formulas.

(Deviation between the ORP of the absorbing fluid and the ORP of the absorbing fluid in a completely oxidized state)=(ORP of the absorbing fluid in a completely oxidized state)−(ORP of the absorbing fluid)

(Preset ORP deviation value)=(ORP of the absorbing fluid in a completely oxidized state as determined from the relationship between known sulfurous acid concentrations and ORP values)−(ORP of the absorbing fluid at a preset sulfurous acid concentration as determined from the relationship between known sulfurous acid concentrations and ORP values)

[Deviation between (deviation between the ORP of the absorbing fluid and the ORP of the absorbing fluid in a completely oxidized state) and (preset ORP deviation value)]=(Deviation between the ORP of the absorbing fluid and the ORP of the absorbing fluid in a completely oxidized state)−(Preset ORP deviation value)

Now, the oxidation controlling method using the above-defined deviation calculating formulas is described below. If the deviation between the ORP of the absorbing fluid and the ORP of the absorbing fluid in a completely oxidized state is greater than the preset ORP deviation value, the opening of control valve 9 is increased to cause an increase in the flow rate of air 6. When the ORP of the absorbing fluid rises as a result of the increase in the flow rate of air 6 and the deviation between the ORP of the absorbing fluid and the ORP of the absorbing fluid in a completely oxidized state becomes less than the preset ORP deviation value, the flow rate of air 6 is decreased. Thus, oxidation is controlled by using, as an index thereto, the deviation between the ORP of the absorbing fluid and the ORP of the absorbing fluid in a completely oxidized state.

EXAMPLES

In order to further illustrate the present invention, an example is given. The composition of an absorbing fluid used to measure the complete oxidation-reduction potential by the passage of air is shown in Table 1. This absorbing fluid has a relatively high manganese concentration (about 30 mg/liter) and hence tends to produce oxidizing substances.

Several methods for the decomposition of peroxides were evaluated by using the absorbing fluid shown in Table 1, and the results thus obtained are shown in Table 2.

TABLE 1

| Temperature | | 50° C. |
|---|---|---|
| Flow rate of air | | 0.3 m$^3$N/h |
| Volume of absorbing fluid in measuring tank | | 2 liters |
| Composition of absorbing fluid | $CaCO_3$ | 1 mol/liter |
| | $CaSO_4$ | 1 mol/liter |
| | $MnSO_4$ | 0.55 mmol/liter |
| | $MgSO_4$ | 50 mmol/liter |

TABLE 2

Results of Evaluation of Several Methods for the Decomposition of Peroxides

| No. | Chemical agent used for the decomposition of peroxides | Decomposition procedure | State of decomposition of peroxides |
|---|---|---|---|
| 1 | Aqueous $H_2O_2$ | Aqueous $H_2O_2$ is added while oxidizing air is being supplied. | Peroxides are scarcely decomposed. The reacted fluid shows no color change (brownish gray). |
| 2 | Aqueous $H_2O_2$ | The supply of oxidizing air is stopped, and aqueous $H_2O_2$ is added. | Peroxides are scarcely decomposed. The reacted fluid shows no color change (brownish gray). |
| 3 | Aqueous $H_2O_2$, $H_2SO_4$ | The supply of oxidizing air is stopped, aqueous $H_2O_2$ is added, and $H_2SO_4$ is then added (in order to reduce the pH temporarily to around 5). | Peroxides seem to have been decomposed. The reacted fluid turns white. |
| 4 | $Na_2SO_3$ | The supply of oxidizing air is stopped, and $Na_2SO_3$ is added. | Peroxides are not decomposed. The reacted fluid shows no color change (brownish gray). |
| 5 | Hydroxylammonium chloride [($NH_3OH$)Cl] [also called hydroxylamine hydrochloride ($NH_2OH.HCl$)] | A hydroxylammonium chloride solution is added while oxidizing air is being supplied. | Peroxides seem to have been decomposed. The reacted fluid turns white. |
| 6 | $SO_2$ | The supply of oxidizing air is stopped, and $SO_2$ gas is passed. | Peroxides seem to have been decomposed. The reacted fluid turns white. |

Next, a comparative example is given. Table 3 shows the results of measurement of the complete oxidation-reduction potential according to a conventional method. Table 4 shows the results of measurement of the complete oxidation-reduction potential according to the method of the present invention which involves the addition of hydrogen peroxide and sulfuric acid.

TABLE 3

| Run No. | Item of measurement | Absorbing fluid | After complete oxidation |
|---|---|---|---|
| 1 | pH (—) | 6.0 | 7.6 |
| | ORP (mV) | 103 | 180 |
| | $SO_3$ concentration (mmol/liter) | 1.2 | <0.1 |
| 2 | pH (—) | 6.0 | 7.9 |
| | ORP (mV) | 290 | 248 |
| | $SO_3$ concentration (mmol/liter) | 0.1 | <0.1 |

TABLE 4

| Run No. | Item of measurement | Absorbing fluid | After complete oxidation |
|---|---|---|---|
| 1 | pH (—) | 6.0 | 8.1 |
| | ORP (mV) | 240 | 140 |
| | $SO_3$ concentration (mmol/liter) | <0.1 | <0.1 |
| 2 | pH (—) | 6.0 | 8.1 |
| | ORP (mV) | 156 | 144 |
| | $SO_3$ concentration (mmol/liter) | 0.6 | <0.1 |

When the above-described reduction procedure prior to the passage of air was omitted, the complete oxidation-reduction potential varied greatly in spite of the fact that the measuring conditions such as the composition of the absorbing fluid and the flow rate of air were kept constant. This made it difficult to determine a preset deviation value between the ORP of the absorbing fluid and the ORP of the absorbing fluid in a completely oxidized state, and eventually caused the COD of waste water to increase from an ordinary value of 7 mg/liter to 30 mg/liter.

We claim:

1. In a flue gas desulfurization process wherein exhaust gas containing sulfur oxides is treated with an absorbing fluid containing a calcium compound, and an oxygen-containing gas is passed through the absorbing fluid containing the resulting calcium sulfite to oxidize the calcium sulfite and thereby form gypsum, a method for measuring oxidation-reduction potential that is adaptable for use with a method for controlling the oxidation of sulfite which comprises the steps of detecting a first deviation signal between the oxidation-reduction potential of the absorbing fluid and the oxidation-reduction potential of the absorbing fluid in a completely oxidized state by means of an oxidation-reduction potential detector equipped with a sample fluid tank for detecting the oxidation-reduction potential of the absorbing fluid and a reference fluid tank for oxidizing the absorbing fluid by the passage of air therethrough and detecting the oxidation-reduction potential of the absorbing fluid in a completely oxidized state, and controlling the flow rate of the oxygen-containing gas in response to a second deviation signal between the first deviation signal and a preset oxidation-reduction potential deviation value, the improvement wherein the oxidation-reduction potential of the absorbing fluid in a completely oxidized state is measured by first decomposing peroxides present in the absorbing fluid with the aid of a chemical agent and thereafter passing air through the absorbing fluid.

2. A method for measuring oxidation-reduction potential in a flue gas desulfurization process as claimed in claim 1 wherein peroxides present in the absorbing fluid are decomposed by adding thereto hydrogen peroxide and then an acid.

3. A method for measuring oxidation-reduction potential in a flue gas desulfurization process as claimed in claim 1 wherein peroxides present in the absorbing fluid are decomposed by using a reducing agent selected from the group consisting of $SO_2$ gas, hydroxylammonium chloride, an aqueous solution of sulfurous acid, a salt of sulfurous acid, and mixtures thereof.

* * * * *